United States Patent
Dominguez et al.

(10) Patent No.: US 9,668,901 B2
(45) Date of Patent: Jun. 6, 2017

(54) INTRAGASTRIC IMPLANTS WITH DUODENAL ANCHORS

(71) Applicant: Apollo Endosurgery, Inc., Austin, TX (US)

(72) Inventors: Zachary Dominguez, Santa Barbara, CA (US); Joseph Raven, Tigard, OR (US); Mitchell H. Babkes, Santa Clarita, CA (US)

(73) Assignee: Apollo Endosurgery US, Inc., Austin, TX (US)

( * ) Notice: Subject to any disclaimer, the term of this patent is extended or adjusted under 35 U.S.C. 154(b) by 282 days.

(21) Appl. No.: 13/938,010

(22) Filed: Jul. 9, 2013

(65) Prior Publication Data

US 2013/0296765 A1   Nov. 7, 2013

Related U.S. Application Data

(63) Continuation of application No. 13/276,174, filed on Oct. 18, 2011, now abandoned.

(60) Provisional application No. 61/394,228, filed on Oct. 18, 2010, provisional application No. 61/485,009, filed on May 11, 2011, provisional application No. 61/394,592, filed on Oct. 19, 2010.

(51) Int. Cl.
*A61F 5/00* (2006.01)

(52) U.S. Cl.
CPC .......... *A61F 5/0033* (2013.01); *A61F 5/0036* (2013.01); *A61F 5/0079* (2013.01)

(58) Field of Classification Search
CPC .................................................. A61F 5/0033
See application file for complete search history.

(56) References Cited

U.S. PATENT DOCUMENTS

| 1,702,974 A | 2/1929 | Macdonald |
| 2,087,604 A | 7/1937 | Mosher |

(Continued)

FOREIGN PATENT DOCUMENTS

| CN | 1250382 A | 4/2000 |
| CN | 1367670 A | 9/2002 |

(Continued)

OTHER PUBLICATIONS

Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

(Continued)

*Primary Examiner* — Tatyana Zalukaeva
*Assistant Examiner* — Sara Sass
(74) *Attorney, Agent, or Firm* — Gordon & Jacobson, P.C.

(57) ABSTRACT

Intragastric fluid transfer devices and related methods for operation thereof are disclosed. The intragastric fluid transfer devices and related methods are intended to assist a patient in maintaining a healthy body weight by stimulating the inner stomach walls and/or the inner duodenum walls. Features of the intragastric fluid transfer device include insertion of the devices transorally and without invasive surgery, without associated patient risks of invasive surgery, and without substantial patient discomfort. The life span of these intragastric fluid transfer devices may be material-dependent upon long-term survivability within an acidic stomach, but is intended to last one year or longer.

20 Claims, 9 Drawing Sheets

(56) References Cited

U.S. PATENT DOCUMENTS

| | | |
|---|---|---|
| 2,163,048 A | 6/1939 | Mckee |
| 2,619,138 A | 11/1952 | Marler |
| 3,667,081 A | 6/1972 | Burger |
| 3,719,973 A | 3/1973 | Bell |
| 3,840,018 A | 10/1974 | Heifetz |
| 3,919,724 A | 11/1975 | Sanders |
| 4,118,805 A | 10/1978 | Reimels |
| 4,364,379 A | 12/1982 | Finney |
| 4,416,267 A | 11/1983 | Garren |
| 4,430,392 A | 2/1984 | Kelley |
| 4,485,805 A | 12/1984 | Foster |
| 4,545,367 A | 10/1985 | Tucci |
| 4,586,501 A | 5/1986 | Claracq |
| 4,592,355 A | 6/1986 | Antebi |
| 4,598,699 A | 7/1986 | Garren |
| 4,607,618 A | 8/1986 | Angelchik |
| 4,636,213 A | 1/1987 | Pakiam |
| 4,648,383 A | 3/1987 | Angelchik |
| 4,694,827 A | 9/1987 | Weiner |
| 4,723,547 A | 2/1988 | Kullas |
| 4,739,758 A | 4/1988 | Lai |
| 4,773,432 A | 9/1988 | Rydell |
| 4,774,956 A | 10/1988 | Kruse |
| 4,844,068 A | 7/1989 | Arata |
| 4,881,939 A | 11/1989 | Newman |
| 4,899,747 A | 2/1990 | Garren |
| 4,925,446 A | 5/1990 | Garay |
| 4,930,535 A | 6/1990 | Rinehold |
| 4,950,258 A | 8/1990 | Kawai |
| 4,969,899 A | 11/1990 | Cox |
| 5,074,868 A | 12/1991 | Kuzmak |
| 5,084,061 A | 1/1992 | Gau |
| 5,211,371 A | 5/1993 | Coffee |
| 5,226,429 A | 7/1993 | Kuzmak |
| 5,255,690 A | 10/1993 | Keith |
| 5,259,399 A | 11/1993 | Brown |
| 5,289,817 A | 3/1994 | Williams |
| 5,308,324 A | 5/1994 | Hammerslag |
| 5,312,343 A | 5/1994 | Krog |
| 5,449,368 A | 9/1995 | Kuzmak |
| 5,514,176 A | 5/1996 | Bosley |
| 5,527,340 A | 6/1996 | Vogel |
| 5,540,701 A | 7/1996 | Sharkey |
| 5,547,458 A | 8/1996 | Ortiz |
| 5,601,604 A | 2/1997 | Vincent |
| 5,658,298 A | 8/1997 | Vincent |
| 5,693,014 A | 12/1997 | Abele |
| 5,725,507 A | 3/1998 | Petrick |
| 5,748,200 A | 5/1998 | Funahashi |
| 5,776,160 A | 7/1998 | Pasricha |
| 5,819,749 A | 10/1998 | Lee |
| 5,820,584 A | 10/1998 | Crabb |
| RE36,176 E | 3/1999 | Kuzmak |
| 5,938,669 A | 8/1999 | Klaiber |
| 6,074,341 A | 6/2000 | Anderson |
| 6,102,678 A | 8/2000 | Peclat |
| 6,102,897 A | 8/2000 | Lang |
| 6,102,922 A | 8/2000 | Jakobsson |
| 6,152,922 A | 11/2000 | Ouchi |
| 6,183,492 B1 | 2/2001 | Hart |
| 6,264,700 B1 | 7/2001 | Kilcoyne |
| 6,290,575 B1 | 9/2001 | Shipp |
| 6,322,538 B1 | 11/2001 | Elbert |
| 6,450,946 B1 | 9/2002 | Forsell |
| 6,454,699 B1 | 9/2002 | Forsell |
| 6,454,785 B2 | 9/2002 | De Hoyos Garza |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,517,515 B1* | 2/2003 | Eidenschink ..... A61M 25/0068 604/101.05 |
| 6,540,789 B1 | 4/2003 | Silverman |
| 6,547,801 B1 | 4/2003 | Dargent |
| 6,579,301 B1 | 6/2003 | Bales |
| 6,629,776 B2 | 10/2003 | Bell |
| 6,675,809 B2 | 1/2004 | Stack |
| 6,682,473 B1 | 1/2004 | Matsuura |
| 6,733,512 B2 | 5/2004 | McGhan |
| 6,733,513 B2 | 5/2004 | Boyle |
| 6,746,460 B2 | 6/2004 | Gannoe |
| 6,776,783 B1 | 8/2004 | Frantzen |
| 6,840,257 B2 | 1/2005 | Dario |
| 6,845,776 B2 | 1/2005 | Stack |
| 6,905,471 B2 | 6/2005 | Leivseth |
| 6,960,233 B1 | 11/2005 | Berg |
| 6,981,978 B2 | 1/2006 | Gannoe |
| 6,981,980 B2 | 1/2006 | Sampson |
| 6,994,095 B2 | 2/2006 | Burnett |
| 7,008,419 B2 | 3/2006 | Shadduck |
| 7,020,531 B1 | 3/2006 | Colliou |
| 7,033,384 B2 | 4/2006 | Gannoe |
| 7,037,344 B2 | 5/2006 | Kagan |
| 7,056,305 B2 | 6/2006 | Garza |
| 7,090,699 B2 | 8/2006 | Geitz |
| 7,214,233 B2 | 5/2007 | Gannoe |
| 7,220,237 B2 | 5/2007 | Gannoe |
| 7,220,284 B2 | 5/2007 | Kagan |
| 7,223,277 B2 | 5/2007 | DeLegge |
| 7,320,696 B2 | 1/2008 | Gazi |
| 7,347,875 B2 | 3/2008 | Levine |
| 7,354,454 B2 | 4/2008 | Stack |
| 7,476,256 B2 | 1/2009 | Meade |
| 7,510,559 B2 | 3/2009 | Deem |
| 7,608,114 B2 | 10/2009 | Levine |
| 7,628,442 B1 | 12/2009 | Spencer |
| 7,682,330 B2 | 3/2010 | Meade |
| 7,695,446 B2 | 4/2010 | Levine |
| 7,699,863 B2 | 4/2010 | Marco |
| 7,753,870 B2 | 7/2010 | Demarais |
| 7,771,382 B2 | 8/2010 | Levine |
| 7,794,447 B2 | 9/2010 | Dann |
| 7,815,589 B2 | 10/2010 | Meade |
| 7,837,643 B2 | 11/2010 | Levine |
| 7,841,503 B2 | 11/2010 | Sonnenschein |
| 7,883,525 B2 | 2/2011 | DeLegge |
| 7,931,693 B2 | 4/2011 | Binmoeller |
| 7,981,162 B2 | 7/2011 | Stack |
| 8,029,455 B2 | 10/2011 | Stack |
| 8,032,223 B2 | 10/2011 | Imran |
| 8,075,582 B2 | 12/2011 | Lointier |
| 8,162,969 B2 | 4/2012 | Brister |
| 8,187,297 B2 | 5/2012 | Makower |
| 8,216,266 B2 | 7/2012 | Hively |
| 2002/0019577 A1 | 2/2002 | Arabia |
| 2002/0055757 A1* | 5/2002 | Torre et al. .................... 606/192 |
| 2002/0095181 A1 | 7/2002 | Beyar |
| 2002/0139208 A1 | 10/2002 | Yatskov |
| 2002/0183782 A1 | 12/2002 | Tsugita |
| 2003/0045896 A1 | 3/2003 | Murphy |
| 2003/0073880 A1 | 4/2003 | Polsky |
| 2003/0074054 A1 | 4/2003 | Duerig |
| 2003/0100822 A1 | 5/2003 | Lew |
| 2003/0106761 A1 | 6/2003 | Taylor |
| 2003/0109935 A1 | 6/2003 | Geitz |
| 2003/0144575 A1 | 7/2003 | Forsell |
| 2003/0153905 A1 | 8/2003 | Edwards |
| 2003/0158570 A1 | 8/2003 | Ferrazzi |
| 2004/0044357 A1 | 3/2004 | Gannoe |
| 2004/0092892 A1 | 5/2004 | Kagan |
| 2004/0117031 A1 | 6/2004 | Stack |
| 2004/0122452 A1 | 6/2004 | Deem |
| 2004/0122453 A1 | 6/2004 | Deem |
| 2004/0143342 A1 | 7/2004 | Stack |
| 2004/0148034 A1 | 7/2004 | Kagan |
| 2004/0172142 A1 | 9/2004 | Stack |
| 2004/0186503 A1 | 9/2004 | DeLegge |
| 2005/0033332 A1 | 2/2005 | Burnett |
| 2005/0049718 A1 | 3/2005 | Dann |
| 2005/0055039 A1 | 3/2005 | Burnett |
| 2005/0085923 A1 | 4/2005 | Levine |
| 2005/0096692 A1 | 5/2005 | Linder |
| 2005/0110280 A1 | 5/2005 | Guy |
| 2005/0131485 A1 | 6/2005 | Knudson |

(56) References Cited

U.S. PATENT DOCUMENTS

| | | |
|---|---|---|
| 2005/0190070 A1 | 9/2005 | Rudduck |
| 2005/0192614 A1 | 9/2005 | Binmoeller |
| 2005/0192615 A1 | 9/2005 | Torre |
| 2005/0197714 A1 | 9/2005 | Sayet |
| 2005/0228504 A1 | 10/2005 | Demarais |
| 2005/0240279 A1 | 10/2005 | Kagan |
| 2005/0250979 A1 | 11/2005 | Coe |
| 2005/0256533 A1 | 11/2005 | Roth |
| 2005/0261711 A1 | 11/2005 | Okada |
| 2005/0267595 A1 | 12/2005 | Chen |
| 2005/0267596 A1 | 12/2005 | Chen |
| 2005/0273060 A1* | 12/2005 | Levy et al. .............. 604/192 |
| 2005/0277975 A1 | 12/2005 | Saadat |
| 2006/0020278 A1 | 1/2006 | Burnett |
| 2006/0025799 A1 | 2/2006 | Basu |
| 2006/0069403 A1 | 3/2006 | Shalon |
| 2006/0106288 A1 | 5/2006 | Roth |
| 2006/0142700 A1 | 6/2006 | Sobelman |
| 2006/0178691 A1 | 8/2006 | Binmoeller |
| 2006/0190019 A1 | 8/2006 | Gannoe |
| 2006/0217762 A1 | 9/2006 | Maahs |
| 2006/0229702 A1 | 10/2006 | Agnew |
| 2006/0252983 A1 | 11/2006 | Lembo |
| 2007/0010864 A1 | 1/2007 | Dann |
| 2007/0016262 A1 | 1/2007 | Gross |
| 2007/0021761 A1 | 1/2007 | Phillips |
| 2007/0078476 A1 | 4/2007 | Hull |
| 2007/0083224 A1 | 4/2007 | Hively |
| 2007/0100368 A1 | 5/2007 | Quijano |
| 2007/0118168 A1 | 5/2007 | Lointier |
| 2007/0135803 A1 | 6/2007 | Belson |
| 2007/0135829 A1 | 6/2007 | Paganon |
| 2007/0147170 A1 | 6/2007 | Hood |
| 2007/0149994 A1 | 6/2007 | Sosnowski |
| 2007/0156013 A1 | 7/2007 | Birk |
| 2007/0156248 A1 | 7/2007 | Marco |
| 2007/0173881 A1 | 7/2007 | Birk |
| 2007/0185374 A1 | 8/2007 | Kick |
| 2007/0185375 A1 | 8/2007 | Stad |
| 2007/0239284 A1 | 10/2007 | Skerven |
| 2007/0250020 A1 | 10/2007 | Kim |
| 2007/0265598 A1 | 11/2007 | Karasik |
| 2007/0276428 A1 | 11/2007 | Haller |
| 2007/0288033 A1 | 12/2007 | Murature |
| 2007/0293716 A1 | 12/2007 | Baker |
| 2008/0015618 A1 | 1/2008 | Sonnenschein |
| 2008/0058840 A1 | 3/2008 | Albrecht |
| 2008/0058887 A1 | 3/2008 | Griffin |
| 2008/0065122 A1 | 3/2008 | Stack |
| 2008/0071305 A1 | 3/2008 | DeLegge |
| 2008/0097513 A1 | 4/2008 | Kaji |
| 2008/0167606 A1 | 7/2008 | Dann |
| 2008/0172079 A1 | 7/2008 | Birk |
| 2008/0208240 A1 | 8/2008 | Paz |
| 2008/0208241 A1 | 8/2008 | Weiner |
| 2008/0221595 A1 | 9/2008 | Surti |
| 2008/0228205 A1 | 9/2008 | Sharkey |
| 2008/0234718 A1 | 9/2008 | Paganon |
| 2008/0234834 A1 | 9/2008 | Meade |
| 2008/0243071 A1 | 10/2008 | Quijano |
| 2008/0243166 A1 | 10/2008 | Paganon |
| 2008/0249635 A1 | 10/2008 | Weitzner |
| 2008/0255601 A1 | 10/2008 | Birk |
| 2008/0255678 A1 | 10/2008 | Cully |
| 2008/0262529 A1 | 10/2008 | Jacques |
| 2008/0306506 A1 | 12/2008 | Leatherman |
| 2009/0012553 A1 | 1/2009 | Swain |
| 2009/0082644 A1 | 3/2009 | Li |
| 2009/0093767 A1 | 4/2009 | Kelleher |
| 2009/0093837 A1* | 4/2009 | Dillon .............. A61B 17/1114 606/191 |
| 2009/0131968 A1 | 5/2009 | Birk |
| 2009/0132031 A1 | 5/2009 | Cook |
| 2009/0143713 A1* | 6/2009 | Van Dam ............ A61B 17/11 604/9 |
| 2009/0149879 A1 | 6/2009 | Dillon |
| 2009/0177215 A1 | 7/2009 | Stack |
| 2009/0198210 A1* | 8/2009 | Burnett ............ A61B 17/12099 604/502 |
| 2009/0216337 A1 | 8/2009 | Egan |
| 2009/0259246 A1 | 10/2009 | Eskaros |
| 2009/0275973 A1 | 11/2009 | Chen |
| 2009/0287231 A1 | 11/2009 | Brooks |
| 2009/0299327 A1 | 12/2009 | Tilson |
| 2009/0299486 A1 | 12/2009 | Shohat |
| 2009/0312597 A1 | 12/2009 | Bar |
| 2010/0030017 A1 | 2/2010 | Baker |
| 2010/0049224 A1 | 2/2010 | Vargas |
| 2010/0081991 A1 | 4/2010 | Swisher |
| 2010/0082047 A1 | 4/2010 | Cosgrove |
| 2010/0087843 A1 | 4/2010 | Bertolote |
| 2010/0100079 A1 | 4/2010 | Berkcan |
| 2010/0100115 A1 | 4/2010 | Soetermans |
| 2010/0121371 A1 | 5/2010 | Brooks |
| 2010/0168782 A1 | 7/2010 | Hancock |
| 2010/0168783 A1 | 7/2010 | Murature |
| 2010/0174307 A1 | 7/2010 | Birk |
| 2010/0198249 A1 | 8/2010 | Sabliere |
| 2010/0234937 A1 | 9/2010 | Wang |
| 2010/0249822 A1 | 9/2010 | Nihalani |
| 2010/0249825 A1 | 9/2010 | Nihalani |
| 2010/0256775 A1 | 10/2010 | Belhe |
| 2010/0256776 A1 | 10/2010 | Levine |
| 2010/0261390 A1 | 10/2010 | Gardner |
| 2010/0274194 A1 | 10/2010 | Sobelman |
| 2010/0286628 A1 | 11/2010 | Gross |
| 2010/0305590 A1 | 12/2010 | Holmes |
| 2010/0331756 A1 | 12/2010 | Meade |
| 2010/0332000 A1 | 12/2010 | Forsell |
| 2011/0009897 A1 | 1/2011 | Forsell |
| 2011/0106113 A1 | 5/2011 | Tavakkolizadeh |
| 2011/0307075 A1 | 12/2011 | Sharma |
| 2012/0022561 A1 | 1/2012 | Forsell |
| 2012/0089172 A1* | 4/2012 | Babkes et al. ............ 606/192 |
| 2012/0095483 A1* | 4/2012 | Babkes et al. ............ 606/153 |
| 2012/0221037 A1 | 8/2012 | Birk |
| 2013/0035711 A1* | 2/2013 | Schwab et al. ............ 606/192 |

FOREIGN PATENT DOCUMENTS

| | | |
|---|---|---|
| DE | 8804765 U1 | 5/1989 |
| DE | 102007025312 A1 | 11/2008 |
| EP | 1396242 A1 | 3/2004 |
| EP | 1396243 A1 | 3/2004 |
| EP | 1397998 A1 | 3/2004 |
| EP | 1774929 A2 | 4/2007 |
| EP | 2095798 | 9/2009 |
| FR | 2797181 A1 | 2/2001 |
| FR | 2823663 A1 | 10/2002 |
| FR | 2852821 A1 | 10/2004 |
| FR | 2855744 A1 | 12/2004 |
| FR | 2892297 A1 | 4/2007 |
| FR | 2941617 A1 | 8/2010 |
| GB | 2086792 A | 5/1982 |
| JP | S63279854 A | 11/1988 |
| JP | 1049572 A | 2/1989 |
| JP | 63264078 | 10/1998 |
| WO | 8800027 | 1/1988 |
| WO | 8800027 A1 | 1/1988 |
| WO | 0015158 A1 | 3/2000 |
| WO | 0032092 | 6/2000 |
| WO | 0110359 A1 | 2/2001 |
| WO | 0149245 A2 | 7/2001 |
| WO | 0166166 A2 | 9/2001 |
| WO | 0235980 A2 | 5/2002 |
| WO | 03055419 A1 | 7/2003 |
| WO | 03105732 A1 | 12/2003 |
| WO | 2004019671 A2 | 3/2004 |
| WO | 2005007231 A1 | 1/2005 |
| WO | 2005094257 A2 | 10/2005 |
| WO | 2005097012 | 10/2005 |
| WO | 2005097012 A2 | 10/2005 |
| WO | 2005110280 | 11/2005 |
| WO | 2005110280 A2 | 11/2005 |

(56) References Cited

FOREIGN PATENT DOCUMENTS

| WO | 2006044640 A1 | 4/2006 |
|---|---|---|
| WO | 2006020370 | 6/2006 |
| WO | 2006063593 A2 | 6/2006 |
| WO | 2006090018 A1 | 8/2006 |
| WO | 2006111961 A2 | 10/2006 |
| WO | 2006118744 A1 | 11/2006 |
| WO | 2007027812 A2 | 3/2007 |
| WO | 2007053556 A1 | 5/2007 |
| WO | 2007076021 A2 | 7/2007 |
| WO | 2007092390 A2 | 8/2007 |
| WO | 2007110866 A2 | 10/2007 |
| WO | 2008101048 A2 | 8/2008 |
| WO | 2008112894 A1 | 9/2008 |
| WO | 2008132745 A2 | 11/2008 |
| WO | 2010042062 A1 | 4/2010 |
| WO | 2010074712 | 7/2010 |
| WO | 2010074712 A2 | 7/2010 |
| WO | 2010087757 A1 | 8/2010 |
| WO | 2010117641 A2 | 10/2010 |

OTHER PUBLICATIONS

Baggio et al. 'Biology of Integrins: GLP-1 and GIP'; Gastroenrology; V. 132; pp. 2131-2157; 2007.

Berne et al; 'Physiology'; V. 5; pp. 55-57, 210, 428, 540, 554, 579, 584, 591; 2004.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Chaudhri; 'Can Gut Hormones Control Appetite and Prevent Obesity?' Diabetes Care; V. 31; Supp 2; pp. S284-S289; Feb. 2008.

Cohen et al.; 'Oxyntomodulin Suppresses Appetite and Reduces Food in Humans'; J. Clin. Endocrinol. Metab.; V. 88; pp. 4696-4701; 2003.

Dakin et al.; 'Oxyntomodulin Inhibits Food Intake in the Rat'; Endocrinology; V. 142; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmocol. Soc; V. 29; pp. 363-366; 1986.

Ekblad et al.; 'Distribution of Pancreatic Peptide and Peptide-YY'; Peptides; V. 23; pp. 251-261;2002.

Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Houpt; 'Gastrointestinal Factors in Hunger and Satiety'; Neurosci. and Behav. Rev.; V. 6; pp. 145-164; 1982.

Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.

Naslund et al.; 'Prandial Subcutaneous Injection of Glucagon-Like Peptide'; Br. J. Nutr.; V. 91; pp. 439-446; 2004.

Renshaw et al. 'Peptide YY: A Potential Therapy for Obesity'; Current Drug Targets; V. 6; pp. 171-179; 2005.

Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.

Wynne et al.; 'Subcutaneous Oxyntomodulin Reduces Body Weight in Overweight and Obese Subjects: A Double-Blind Randomized, Controlled Trial': Diabetes; V. 54; pp. 2390-2395; 2005.

BIB Bioenterics Intragastric Balloon Program, 'Take Control of Your Weight and Your Life/The Solution for You,' Inamed Health, pp. 1-2; Jan. 19, 2004.

BIB Bioenterics Intragastric Balloon Program, 'Taking the Next Step/Take Control of Your Weight and Your Life,' Inamed Health, pp. 1-9; Apr. 29, 2004.

BIB Data Sheet Directions for Use, 'BioEnterics Intragastric Balloon System,' Inamed Health, 1-12 pp.

'Living With the Bib/BioEnterics Intragastric Balloon Program,' Inamed Health; 1-10 Patient Information Brochure; pp.; May 1, 2005.

* cited by examiner

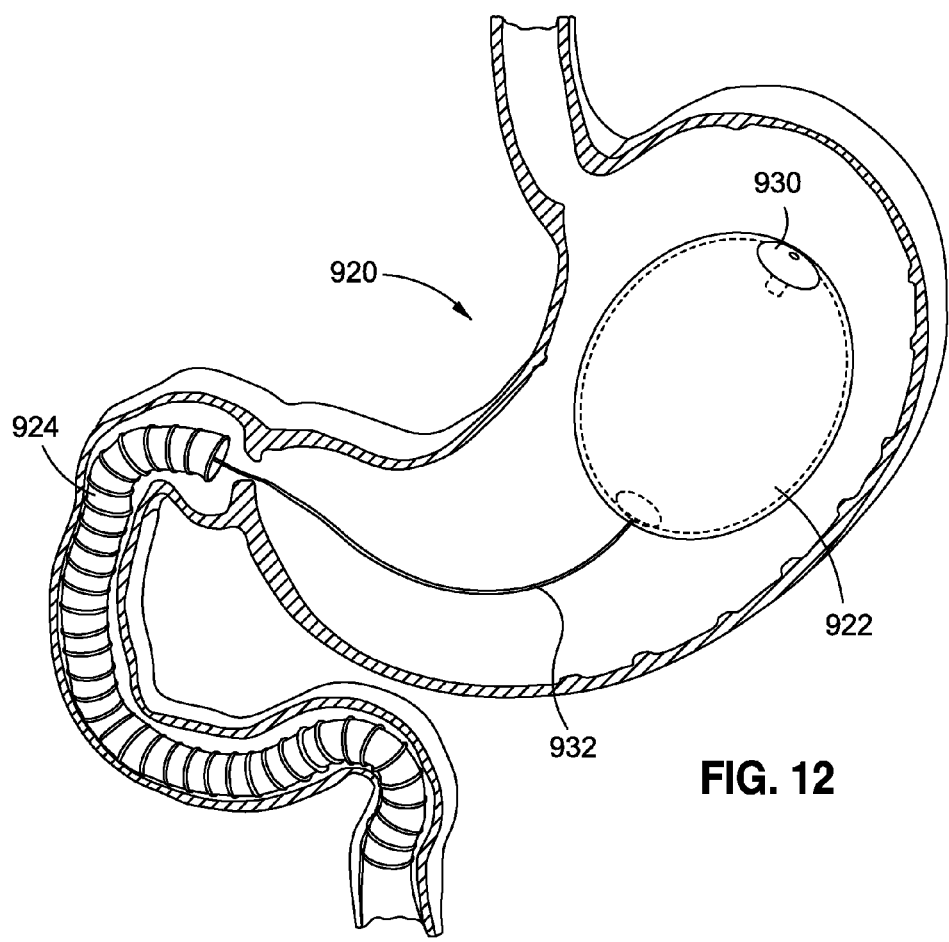
FIG. 12
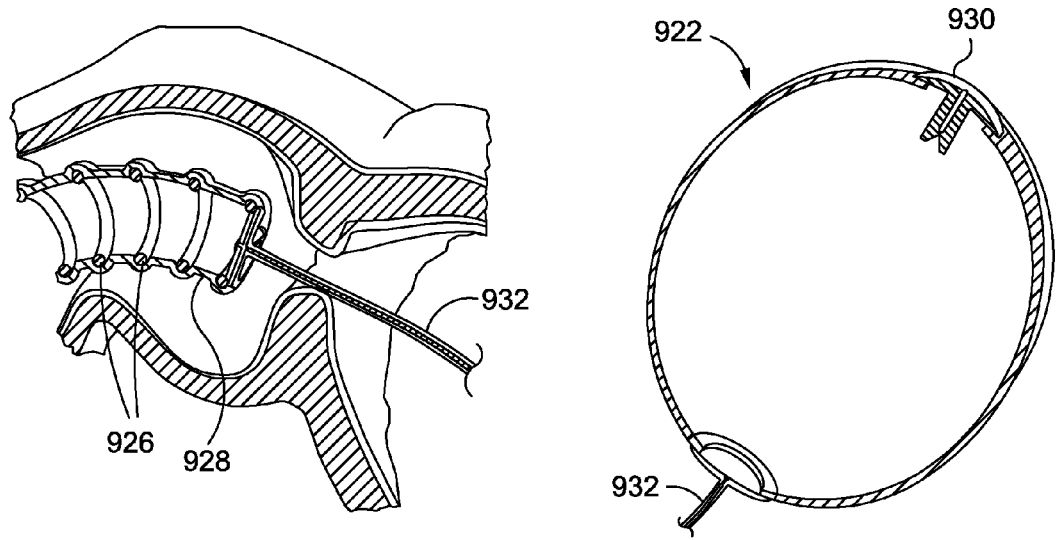
FIG. 13A   FIG. 13B

INTRAGASTRIC IMPLANTS WITH DUODENAL ANCHORS

RELATED APPLICATIONS

The present application is a continuation of U.S. patent application Ser. No. 13/276,174, filed Oct. 18, 2011, which claims priority under 35 U.S.C. §119 to U.S. Provisional Application No. 61/394,228, filed Oct. 18, 2010, to U.S. Provisional Application No. 61/485,009, filed May 11, 2011, and to 61/394,592, filed Oct. 19, 2010, the disclosures of which are incorporated by reference herein.

FIELD OF THE INVENTION

The present invention generally relates to medical systems, apparatus and uses thereof for treating obesity and/or obesity-related diseases, and more specifically, relates to intragastric fluid transfer devices designed to treat obesity.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States is projected to reach approximately 400,000 annually by 2010.

Examples of surgical methods and devices used to treat obesity include the LAP-BAND® (Allergan Medical of Irvine, Calif.) gastric band and the LAP-BAND AP® (Allergan). However, surgery might not be an option for every obese individual; for certain patients, non-surgical therapies or minimal-surgery options are more effective or appropriate.

Intragastric balloons are also well known in the art as a means for treating obesity. One such inflatable intragastric balloon is described in U.S. Pat. No. 5,084,061 and is commercially available as the Orbera® System from Allergan Medical of Irvine, Calif. These devices are designed to provide therapy for moderately obese individuals who need to shed pounds in preparation for surgery, or as part of a dietary or behavioral modification program.

The Orbera® System, for example, consists of a silicone elastomer intragastric balloon that is inserted into the stomach in an empty or deflated state and thereafter filled (fully or partially) with a suitable fluid. The balloon occupies space in the stomach, thereby leaving less room for food and creating a feeling of satiety for the patient. Placement of the intragastric balloon is non-surgical, trans-oral, usually requiring no more than 20-30 minutes. The procedure is performed gastroscopically in an outpatient setting, typically using local anesthesia and sedation. Intragastric balloons typically are implanted for a finite period of time, up to six months. Removing the balloon requires deflation by puncturing with a gastroscopic instrument, and either aspirating the contents of the balloon and removing it, or allowing the fluid to pass into the patient's stomach. Clinical results with these devices show that for many obese patients, the intragastric balloons significantly help to control appetite and accomplish weight loss.

Some attempted solutions for weight loss by placing devices in the stomach result in unintended consequences. For instance, some devices tend to cause food and liquid to back up in the stomach, leading to symptoms of gastroesophageal reflux disease (GERD), a condition in which the stomach contents (food or liquid) leak backwards from the stomach into the esophagus. Also, the stomach acclimates to some gastric implant devices, leading to an expansion of stomach volume and consequent reduction in the efficacy of the device.

However, none of these devices provide for intraduodenal stimulation. Intraduodenal pressures may further aid a patient in achieving weight loss and fighting obesity. Indeed, what is needed is a device that provides both intragastric and intraduodenal benefits to assist a patient to lose weight.

SUMMARY OF THE INVENTION

An intragastric fluid transfer device that advantageously induces weight loss in a patient in one or more ways including those described herein. The intragastric fluid transfer device functions as a volume occupying device in the patient's stomach, thereby reducing food ingested during a meal and reducing the sensation of pre-prandial hunger. Additionally, the portion of the intragastric fluid transfer device residing inside the patient's duodenum may sufficiently alter the antroduodenal pressure gradient to slow gastric emptying, thereby reducing the total volume of food ingested during a meal and inducing cessation of feeding at an earlier time-point during the meal. Further additionally, the portion of the intragastric fluid transfer device residing inside the patient's duodenum may slow the passage of ingested food through the proximal duodenum, thereby leading to a mechanical slowing of gastric content released into the proximal small intestine.

In one advantageous aspect, the intragastric fluid transfer device utilizes naturally occurring and transient stomach contractions to trigger a sustained change in the device, which results in a physiological response that may result in patient weight loss. Moreover, the feeling of satiety caused by the intra-duodenal balloon is frequently temporally aligned with the patient's consumption of meals such that the patient begins to associate the two events (i.e., eating a meal and feeling satiated).

The advantageous intragastric fluid transfer device providing the benefits described herein generally allows for easy and quick placement and removal. Surgery is usually not required or very minimal.

In one embodiment, the intragastric fluid transfer device may reside in the lower stomach, the pylorus and the duodenum of a patient and may include a gastric balloon, a tether, and an intra-duodenal balloon. The gastric balloon of the intragastric fluid transfer device may predominantly remain in the lower stomach region while the intra-duodenal balloon predominantly remains in the duodenum region. The tether may act as a fluid conduit between the gastric balloon and the intra-duodenal balloon.

An implantable device of the present application that is configured to be placed in a patient's stomach and duodenum region transorally without surgery to treat and prevent obesity comprises a gastric balloon residing in the patient's stomach and formed of a material that can withstand the acidic environment of the patient's stomach for at least 6 months. The inflated gastric balloon has an inflated volume sufficient ensure that the gastric balloon cannot pass through patient's pylorus. An intra-duodenal balloon having a deflated volume that will fit within the patient's duodenum and allow food to pass and an inflated volume that contacts the walls of the duodenum couples to the gastric balloon via a fluid transfer conduit. The device further may comprise a first valve, such as a duckbill valve, located between the gastric balloon and intra-duodenal balloon and configured to allow fluid to flow freely from the gastric balloon to the fluid transfer conduit and limit backflow. The first valve may be configured to limit backflow back into the gastric balloon to 0.2 cubic centimeters per hour. The device may also include a flow restrictor located between the gastric balloon and intra-duodenal balloon and configured to allow fluid to flow from the intra-duodenal balloon to the gastric balloon only when the pressure within the intra-duodenal balloon exceeds the pressure within the gastric balloon. Preferably, the flow restrictor limits flow back into the gastric balloon to a flow rate of between 0.1 µL per hour to about 1 L per hour. In one embodiment, the gastric balloon is configured to maintain a volume of 200 milliliters or more to prevent the gastric balloon from migrating into a pylorus region of the patient. The gastric balloon may have an uneven surface feature that provides stimulation to the stomach walls.

A passive intragastric obesity treatment implant disclosed herein features a series of inflatable members connected together with intermediate tethers, each of the inflatable members having alternating ribs and grooves on their external surfaces. The inflatable members each have a size that will not pass through the pyloric sphincter and together take up volume within the stomach of at least 400 ml and are made of a material that will resist degradation over a period of at least six months within the stomach. A duodenal anchor connects to a distal inflatable member with a distal tether, has a size that permits it to pass through the pyloric sphincter, and is formed of a material of sufficient mass and specific gravity that prevents it from migrating back up through the pyloric sphincter. A proximal inflatable member desirably includes an internally threaded sleeve suitable for receiving an externally threaded end of a delivery tube. The intermediate tethers are preferably tubular permitting passage of a stiff rod through the series of inflatable members. The distal tether may have a heat formed distal end and a second heat formed bead just proximal to the steel ball to retain the steel ball thereon.

Another aspect of the present application is a passive intragastric obesity treatment implant comprising an expandable frame formed of a plurality of longitudinal struts and having an expanded diameter sufficient to prevent passage through the pyloric sphincter. A tether connects to a distal end of the frame, and a duodenal anchor connects to one end of the umbrella member. The duodenal anchor has a size that permits it to pass through the pyloric sphincter and is formed of a material of sufficient mass and specific gravity that prevents it from migrating back up through the pyloric sphincter. The implant is formed of a material which permits it to be compressed into a substantially linear delivery configuration and that will resist degradation over a period of at least six months within the stomach. The frame in its expanded state may have an oblong shape. The duodenal anchor preferably comprises a stainless steel ball.

In one form, the frame has a hollow threaded proximal end to which an obturator may attach for delivering and removing the frame.

A still further passive intragastric obesity treatment implant of the present application has an inflatable member having an inflated size sufficient to occupy space within the stomach and preventing passage down the pylorus or back up through the esophageal sphincter. A duodenal sleeve for positioning in the duodenum and reinforced to prevent kinking attaches to the inflatable member via a tether. The implant is formed of a material which permits it to be compressed into a substantially linear delivery configuration and that will resist degradation over a period of at least six months within the stomach. The inflatable member further may include a valve member for filling and emptying the member with a fluid. The duodenal sleeve preferably comprises a flexible sleeve wall reinforced by a plurality of spaced loops. The tether may comprise a strong inner member coated with a material that resists degradation in the stomach.

A method described herein for treating and prevent obesity uses an intragastric fluid transfer device and comprises inflating a gastric balloon residing in a patient's stomach with fluid. The method includes deflating the gastric balloon in response to contractions of the patient's stomach, and inflating an inflatable member residing in a patient's duodenum in response to deflating the gastric balloon. The method may further comprise inflating the gastric balloon in response to the contractions of the patient's stomach stopping, and deflating the inflatable member in response to the contractions of the patient's stomach stopping. The method also involve stopping the inflating or deflating of the gastric balloon when a pressure equilibrium between the gastric balloon and the inflatable member is reached, as well as stopping the inflating or deflating of the inflatable member when a pressure equilibrium between the gastric balloon and the inflatable member is reached.

The gastric balloon may be fluid filled (e.g., saline filled). If the inner stomach walls of the patient exerts a pressure on the gastric balloon (e.g., during stomach contractions when the patient is consuming food), the pressure exerted on the gastric balloon may cause fluid or air within the gastric balloon to be transferred via the tether to the intra-duodenal balloon residing in the duodenum. In this way, the intra-duodenal balloon begins to inflate and expand, and as a result may increase pressure on the patient's duodenum thereby allowing the patient to feel more satiated.

Once the stomach contractions cease or if the stomach contractions cannot provide enough force to generate pressure to drive fluid into the intra-duodenal balloon, the fluid may stop flowing into the intra-duodenal balloon. And when the pressure in the gastric balloon begins to decrease, fluid may flow back from the intra-duodenal balloon back to the gastric balloon thereby deflating the intra-duodenal balloon and inflating the gastric balloon. In one embodiment, fluid from the gastric balloon may flow into the tether via a valve and from the tether into the gastric balloon via a flow restrictor.

In one embodiment, the surface of the gastric balloon, the tether and the intra-duodenal balloon may be smooth. Alternatively, the outside surface of the gastric balloon, and/or the outside surface of the intra-duodenal balloon, and/or the outside surface of the tether may be textured or otherwise not uniformly smooth. The present invention also encompasses an implantable device for the treatment of obesity, the device comprising: (a) a inflatable intragastric gastric balloon made at least in part of an acid resistant material (i.e.

the shell) and constructed for placement in a patient's stomach, so that once inflated the inflated intragastric gastric balloon has an inflated volume sufficient to ensure that the gastric balloon cannot pass through the patient's pylorus; (b) an inflatable intra-duodenal balloon having a deflated volume that permits the intra-duodenal balloon to be easily placed within the patient's duodenum and yet at the same time still allow food and/or fluids to pass through the duodenum, and when inflated the intra-duodenal has a volume such that a wall of the intra-duodenal balloon securely contacts a wall of the duodenum so as to impede or prevent food and/or fluid flow through the duodenum, and; (c) a fluid transfer conduit providing a conduit for between the gastric balloon and intra-duodenal balloon of the device.

BRIEF DESCRIPTION OF THE DRAWINGS

The following detailed descriptions are given by way of example, but not intended to limit the scope of the disclosure solely to the specific embodiments described herein, may best be understood in conjunction with the accompanying drawings in which:

FIGS. 12 and 13A-13B shows a further intragastric device implanted in the stomach with an inflated balloon tethered to a ribbed duodenal sleeve.

DETAILED DESCRIPTION OF THE PREFERRED EMBODIMENTS

Figure 1:
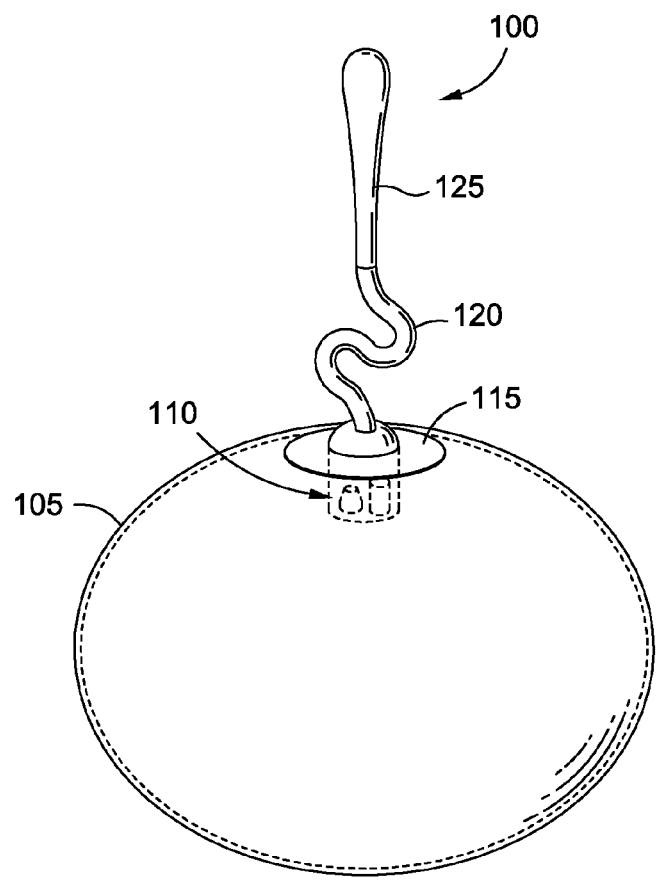
FIG. 1 illustrates a perspective view of the intragastric fluid transfer device in accordance with one or more embodiments described herein.

Persons skilled in the art will readily appreciate that various aspects of the disclosure may be realized by any number of methods and devices configured to perform the intended functions. Stated differently, other methods and devices may be incorporated herein to perform the intended functions. It should also be noted that the drawing FIGS. referred to herein are not all drawn to scale, but may be exaggerated to illustrate various aspects of the invention, and in that regard, the drawing FIGS. should not be construed as limiting. Finally, although the present disclosure may be described in connection with various medical principles and beliefs, the present disclosure should not be bound by theory.

By way of example, the present disclosure will reference certain intragastric fluid transfer devices. Nevertheless, persons skilled in the art will readily appreciate that the present disclosure advantageously may be applied to one of the numerous varieties of intragastric fluid transfer devices.

In one embodiment, these intragastric fluid transfer devices described herein are intended to be placed inside the patient, transorally and without invasive surgery, without associated patient risks of invasive surgery and without substantial patient discomfort. Recovery time may be minimal as no extensive tissue healing is required. The life span of these intragastric fluid transfer devices may be material-dependent upon long-term survivability within an acidic stomach, but is intended to last six months or longer.

Certain aspects of the present application are directed to a variety of different intragastric devices that passively treat obesity by taking up space within the stomach or contact areas in and around the stomach to induce feelings of satiety. Furthermore, some devices described herein affect the rate of stomach emptying. It should be understood that a number of the disclosed devices provide more than one of these passive aspects, and also that any disclosed structure could be combined with another disclosed structure unless physically impossible. As such, combinations of the satiety-inducing features disclosed herein, even if not explicitly stated, are contemplated. It should be noted that the term "passive" refers primarily to a lack of any moving parts within the devices, but in general to the inert nature of the various devices. A passive device as defined herein, however, is not one that cannot affect change or stimulate the stomach, but rather one that may do so without any physical or chemical changes to its basic makeup.

FIG. 1A illustrates an intragastric fluid transfer device 100. The intragastric fluid transfer device 100 may include a gastric balloon 105, a fluid transfer component housing 110, a supporting flange 115, a tether 120 and an intra-duodenal balloon 125. As shown, the gastric balloon 105 may be attached to the intra-duodenal balloon 125 via the tether 120. The supporting flange 115 attaches to one side of the gastric balloon and physically supports and fixes the connection point between the gastric balloon 105 and the tether 120. The supporting flange 115 spreads out stresses imparted on the balloon 105. One end of the tether 120 may be attached to the gastric balloon 105 proximal to the fluid transfer component housing 110 and the other end of the tether 120 may be attached to the intra-duodenal balloon 125. In one embodiment, the tether 120 may be hollow and may be configured to allow fluid to travel from the gastric balloon 105 to the intra-duodenal balloon 125 and vice versa. In one embodiment, the combined fluid within the intragastric fluid transfer device 100 (e.g., inside the gastric balloon 105, the tether 120 and the intra-duodenal balloon 125) may be constant. However, the fluid inside any one of these components may vary depending on the pressure exerted on the intragastric fluid device 100 and other factors.

In one embodiment, the gastric balloon 105 may be constructed out of rubbers, fluorosilicones, fluoroelastomers, thermoplastic elastomers, or any combination thereof, in addition to any other appropriate material. The materials discussed herein advantageously allow the gastric balloon 105 to withstand the acidic environment of the patient's stomach for 6 months or more. The gastric balloon 105 may act as a volume occupying device and may be located inside the patient's stomach. Additionally, the gastric balloon 105 may further act as a reservoir from where fluid is transferred to the intra-duodenal balloon 125 during, for example, stomach contractions.

In another embodiment, while the fluid volume of the gastric balloon 105 is variable, it may be configured such that it never drops below a threshold. For example, the gastric balloon 105 may be configured to stay above a volume of 200 mL to ensure that it is prevented from migrating into the patient's pylorus.

Turning to the intra-duodenal balloon 125 of the intragastric fluid transfer device 100, one function of the intra-duodenal balloon 125 is to exert pressure on the patient's duodenum when the intra-duodenal balloon 125 is inflated with fluid from the gastric balloon 105. More particularly, by exerting a set of pressures on the inner walls of the patient's duodenum, the nervous system of the patient may interpret the pressures as a signal to slow gastric emptying. In other words, via mechanical and physiological means, slowing of the gastric emptying may be achieved and the patient may feel satiated for a longer period of time.

In one embodiment, the intra-duodenal balloon 125 may be constructed out of rubbers, fluorosilicones, fluoroelastomers, thermoplastic elastomers, thermoplastics, thermosets, metals, glass or any combination thereof, in addition to any other appropriate material.

Similarly, the tether 120 connecting the gastric balloon 105 and the intra-duodenal balloon 125 may be constructed out of the same or similar list of materials as the intra-duodenal balloon 125, and provides a fluid conduit between the gastric balloon 105 and the intra-duodenal balloon 125. Here, the tether 120 may be rigid or flexible, and may range from a length of about 1 millimeter to about 1 meter. The diameter of the tether 120 may range from about 1 millimeter to about 5 centimeters.

Figure 2:
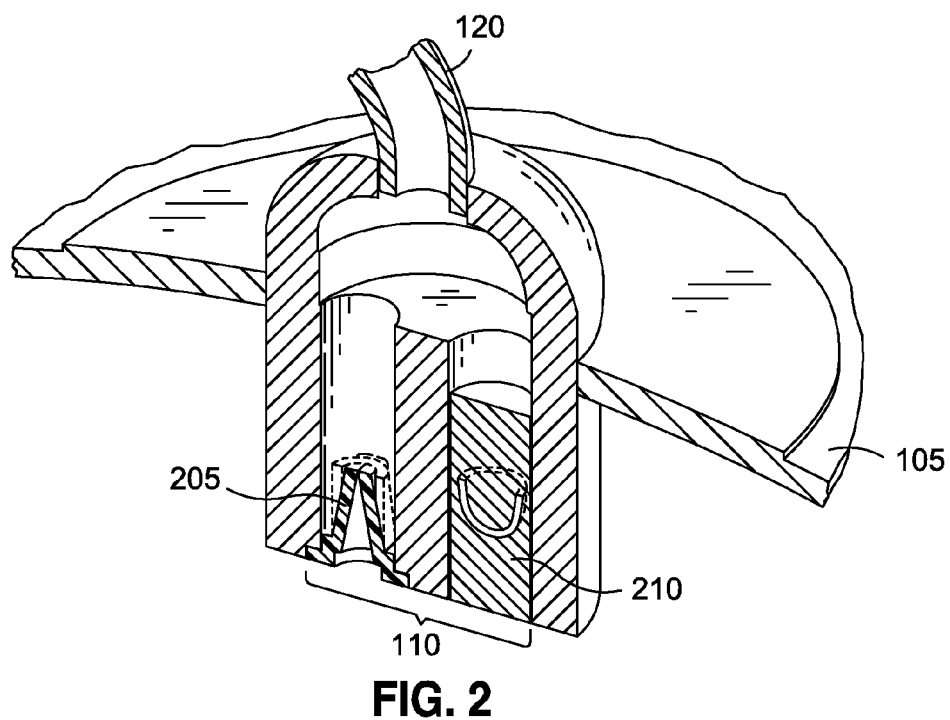
FIG. 2 illustrates a close up view of a valve and a flow restrictor inside the intragastric fluid transfer device in accordance with one or more embodiments described herein.

FIGS. 1 and 2 show the fluid transfer component housing 110 to be located in the gastric balloon 105, and specifically within the fluid transfer component housing 110, which preferably comprises a dome-shaped rigid member. In another embodiment, the tether 120 may also house the fluid transfer components (e.g., the duckbill valve 205 and the flow restrictor 210 of FIG. 2). Or, the duckbill valve 205 and the flow restrictor 210 may even be located proximal to the connection point between the tether 120 and the intra-duodenal balloon 125, such as entirely within the gastric balloon 105.

FIG. 2 shows a close up illustration of the fluid transfer components of FIG. 1. In general, the fluid transfer components are configured to allow for liquid or gas transfer from the gastric balloon 105 and the intra-duodenal balloon 125. Furthermore, the fluid transfer components regulate the flow of fluids from the intra-duodenal balloon 125 back to the gastric balloon 105. In one embodiment, the rate of flow from the intra-duodenal balloon 125 back to the gastric balloon 105 may be configured to be between about 0.1 μL per hour to about 1 L per hour.

As shown, the fluid transfer components 110 may include a duckbill valve 205 and a flow restrictor 210. The "beak" of valve 205 resides inside the gastric balloon 105 and points towards the tether 120. By employing a duckbill valve 205, fluid may travel from inside the gastric balloon 105 to the tether 120 and ultimately to the intra-duodenal balloon 125. Here, the duckbill valve 205 may be configured to have a cracking pressure between about 0.1 mmHg to about 1000 mmHg in order to optimize the effect of the stomach's contraction on the gastric balloon 105. As fluid flows across the duckbill valve 205 into the tether 120 and the intra-duodenal balloon 125, the duckbill valve 205 may function to prevent backflow back into the gastric balloon 105. In one embodiment, the backflow may be limited to about 0.2 cc per hour through the duckbill valve 205.

As shown in FIG. 2, the flow restrictor 210 functions to allow fluid to flow from the tether 120 and the intra-duodenal balloon 125 of FIG. 1 back inside the gastric balloon 105. However, the flow rate of the fluid back inside the gastric balloon 105 might not be as fast as the flow rate of fluid moving from the gastric balloon 105 into the tether 120 and the intra-duodenal balloon 125. In one example, it may take upwards of 12 hours for all the fluid to move from outside the gastric balloon 105 back into the gastric balloon 105 through the flow restrictor 210. Advantageously, this causes the patient to feel a prolonged experience of fullness, gastric emptying and satiety.

In one embodiment, the flow restrictor 210 may also be a valve. Alternatively, the flow restrictor 210 may be a "loose plug" that significantly slows, but still allows fluid to travel from the tether 120 to the inside of the gastric balloon 105. Alternatively, the flow restrictor 210 may be a very small hole, which limits the rate of flow of fluid from the tether 120 to the inside of the gastric balloon 105. In one embodiment, the flow restrictor 210 is uni-directional (e.g., a one-way opening or valve) in the sense that it only allows fluid to travel from the tether 120 to the inside of the gastric balloon 105 and does not allow fluid to travel from the gastric balloon 105 to the tether 120. Alternatively, the flow restrictor 210 may be bi-directional allowing flow to and from the tether 120 into and out of the intra-duodenal balloon 125, respectively. In one embodiment, the duckbill valve 205 and the flow restrictor 210 may be constructed out of rubbers, fluorosilicones, fluoroelastomers, thermoplastic elastomers, thermoplastics, thermosets, metals, glass or any combination thereof, in addition to any other appropriate material. Regardless of the material used to construct the duckbill valve 205 and the flow restrictor 210, the location of the pressure exerted on and the pressure within the intragastric fluid transfer device 100 control the flow of fluid between the gastric balloon 105 and the intra-duodenal balloon 125.

Figure 3:
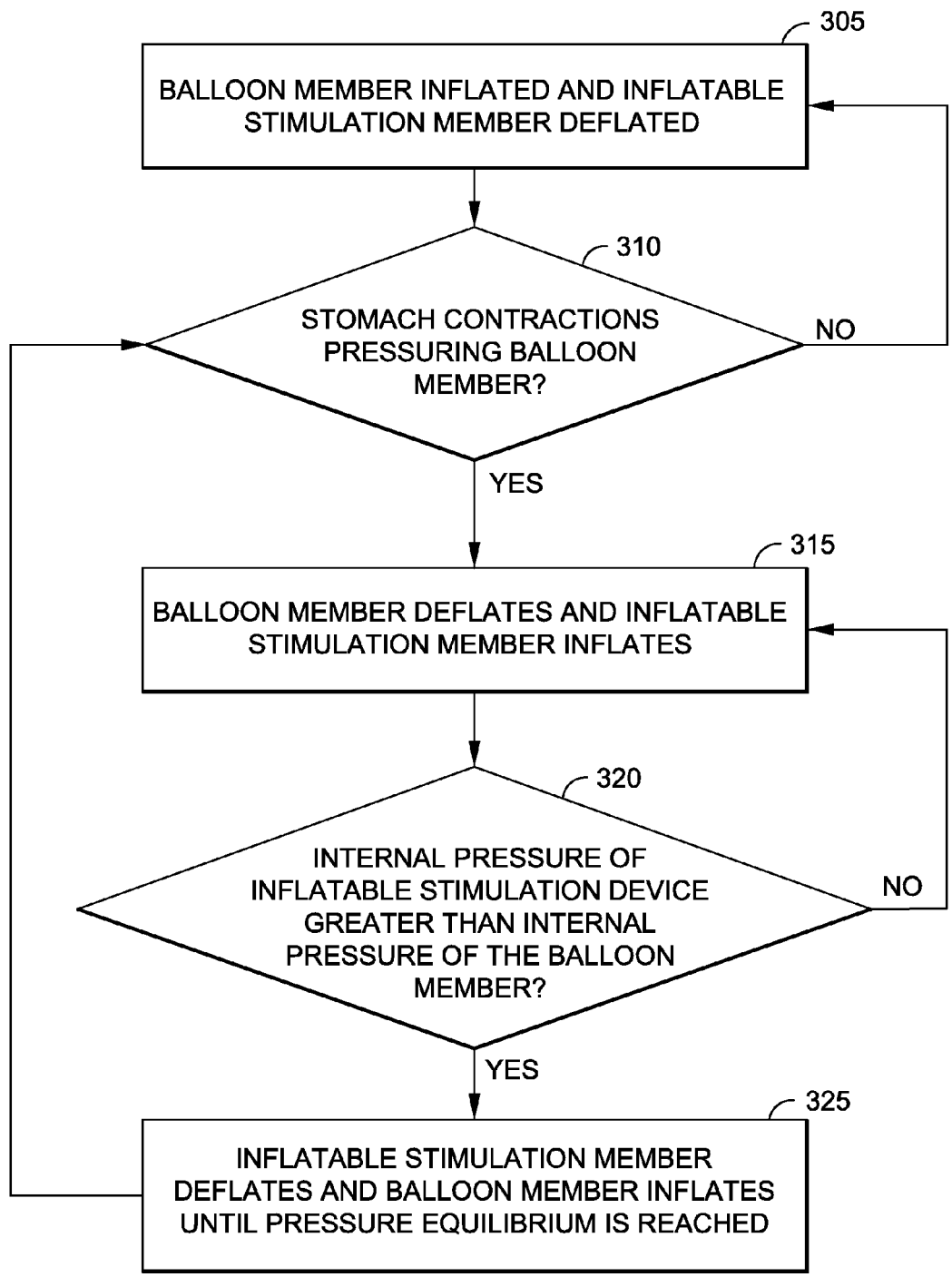
FIG. 3 illustrates a flow chart of a method of operating the intragastric fluid transfer device in accordance with one or more embodiments described herein.

FIG. 3 is a flow chart illustrating an example of the operation of the intragastric fluid transfer device 100. Initially, at step 305, the gastric balloon 105 may be inflated and filled with fluid, while the intra-duodenal balloon 125 might not be as inflated and filled with fluid. At step 310, stomach contractions pressuring the gastric balloon 105 may trigger step 315, where the gastric balloon 105 of the intragastric fluid transfer device 100 may begin to deflate and that fluid may be transferred to the intra-duodenal balloon 125 (which begins to inflate). Next, at step 320, if the pressure in the intra-duodenal balloon 125 becomes greater than the pressure inside the gastric balloon 105 (e.g., when the stomach stops contracting), the fluid begins to flow from the intra-duodenal balloon 125 back to the gastric balloon 105, and the process reverts back to step 310 and waits for stomach contractions to pressure the gastric balloon 105. If no stomach contractions are detected at step 310, then the gastric balloon 105 and the intra-duodenal balloon 125 remain as is.

More particularly, when a pressure is exerted on the exterior of the gastric balloon 105 (e.g., via stomach contractions), the internal pressure of the gastric balloon 105 is increased and causes or triggers fluid to flow from the gastric balloon 105 to the intra-duodenal balloon 125. However, once the stomach contractions lessen or stop, pressure is lessened and/or pressure is no longer exerted on the exterior of the gastric balloon 105, and now the pressure is greater in the intra-duodenal balloon 125. Accordingly, the pressure begins to equalize between the gastric balloon 105 and the intra-duodenal balloon 125, and fluid is transferred from the intra-duodenal balloon 125 back into the gastric balloon 105.

Figures 4A, 4B, 4C:
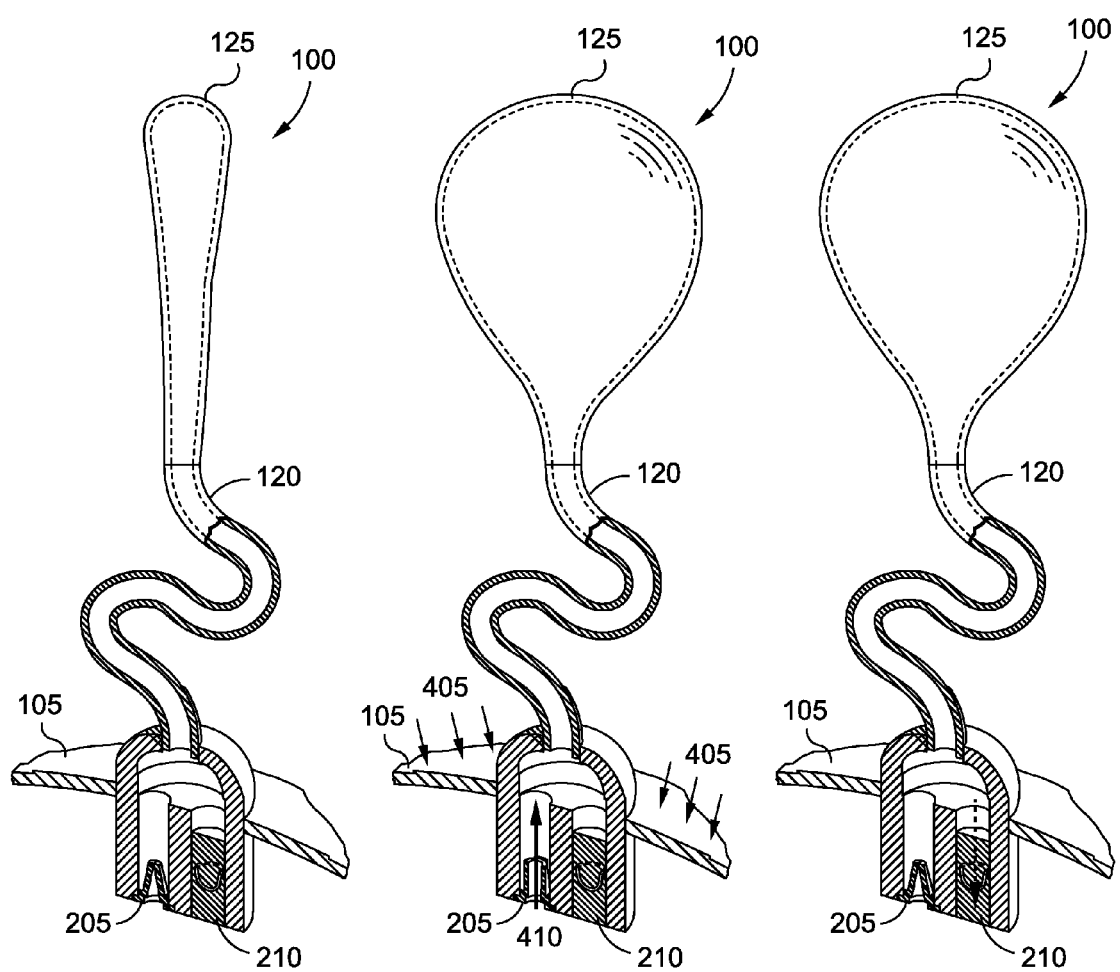
FIG. 4A illustrates a deflated state of the intra-duodenal balloon of the intragastric fluid transfer device in accordance with one or more embodiments described herein.
FIG. 4B illustrates an inflated state of the intra-duodenal balloon of the intragastric fluid transfer device and stomach contractions in accordance with one or more embodiments described herein.
FIG. 4C illustrates an inflated state of the intra-duodenal balloon of the intragastric fluid transfer device and a direction of fluid flow in accordance with one or more embodiments described herein.

FIGS. 4A-4C illustrate the different inflation states of the intragastric fluid transfer device 100 in relation to fluid flow direction and may further illustrate a sequence of events during a stomach contraction. FIG. 4A illustrates the intragastric fluid transfer device 100 of FIG. 1 in an equilibrium state with little or no pressure exerted by the stomach (e.g., when the stomach is in a resting state and/or during gastric relaxation) on the gastric balloon 105. Here, the pressure in the gastric balloon 105 may equal the pressure in the inflatable intra-duodenal balloon 125. FIG. 4B illustrates the intragastric fluid transfer device 100 of FIG. 1 when the stomach begins to contract as illustrated by arrows 405. As shown, a pressure gradient is created, forcing fluid through the duckbill valve 205 (shown by arrow 410) and into the tether 120 and the intra-duodenal balloon 125 (which appears to be inflated), thereby creating pressure or strain on the inside walls of the patient's duodenum. Once, the stomach contractions end or become less frequent (e.g., when the patient stops eating), the pressure in the intra-duodenal balloon 125 begins to cause the fluid to flow through the flow restrictor 210 and back into the gastric balloon 105 as shown in FIG. 4C. The process of relieving pressure in the intra-duodenal balloon 125 may be configured and may take any amount of time between about 1 minute and about 12 hours. In one embodiment, the pressure in the gastric balloon 105 and the intra-duodenal balloon 125 may vary depending on stomach contractions and other pressures exerted on the intragastric fluid transfer device 100. That is, a pressure in the gastric balloon 105 may be higher in some situations (e.g., when the stomach begins contracting), and a pressure in the intra-duodenal balloon 125 may be higher (e.g., after a long period of stomach contractions just before the stomach ceases contractions).

The primary purpose of the intra-duodenal balloon component is to exert pressure on the duodenum. Depending on the embodiment of this component, it may be manufactured from materials including (but not limited to) rubbers, fluorosilicones, fluoroelastomers, thermoplastic elastomers, thermoplastics, thermosets, metals, glass, or any combinations thereof. This component is used to exert a pressure on the walls of duodenum and to slow gastric emptying through mechanical and physiological means. The pressures of the stomach and duodenum are monitored by the body, via neural mechanoreception. The device is intended to produce a set of pressures that will be interpreted by the nervous system as a signal to slow gastric emptying.

Figure 5A:
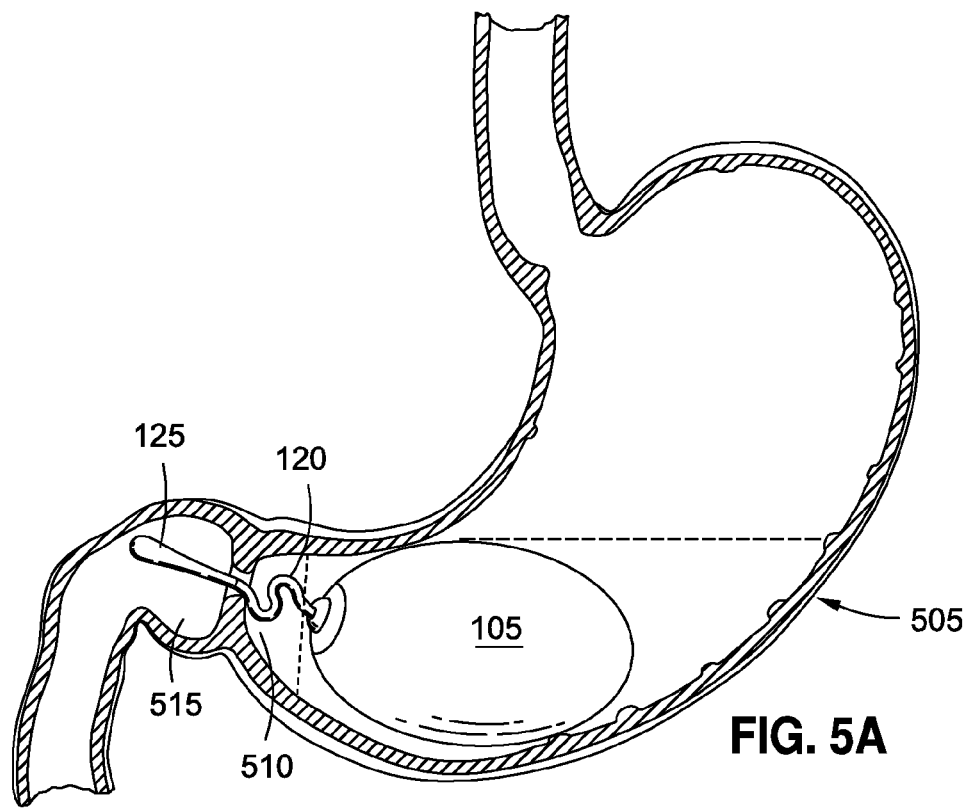
FIG. 5A illustrates a deflated state of the intra-duodenal balloon and an inflated state of the gastric balloon of the intragastric fluid transfer device in accordance with one or more embodiments described herein.
Figure 5B:
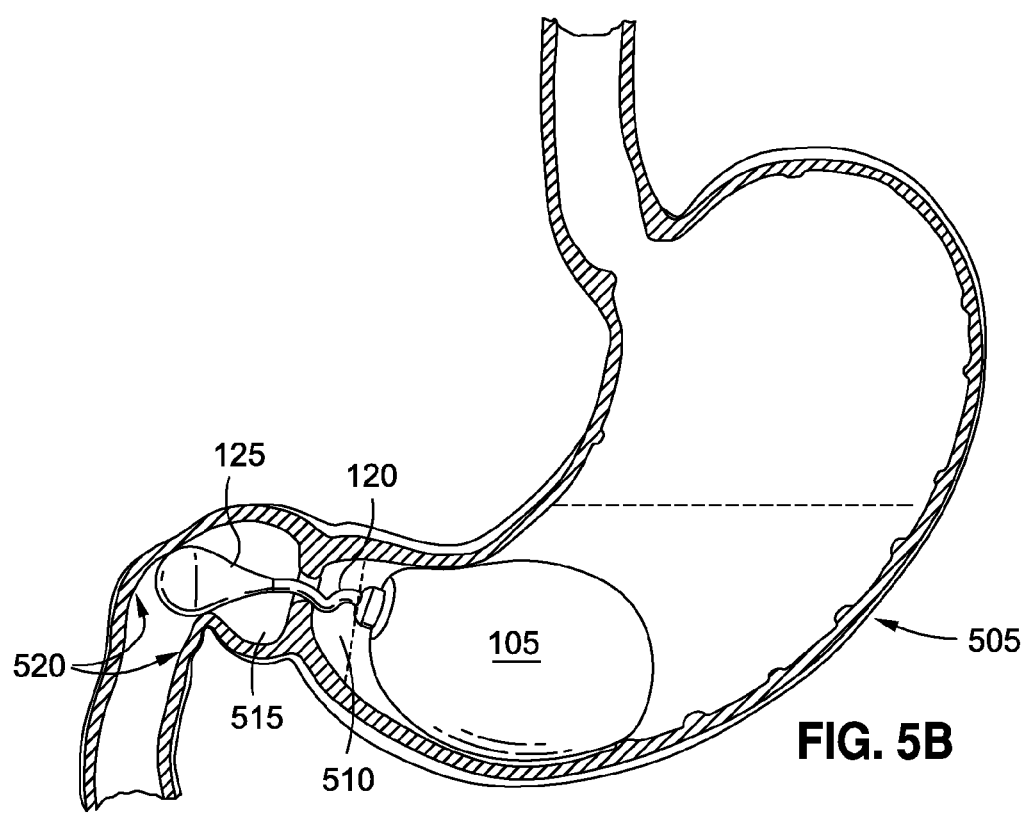
FIG. 5B illustrates an inflated state of the intra-duodenal balloon and a deflated state of the gastric balloon of the intragastric fluid transfer device in accordance with one or more embodiments described herein.

FIGS. 5A and 5B illustrate the intragastric fluid transfer device 100 of FIG. 1A placed inside the patient's stomach region. As shown, the gastric balloon 105 resides in the lower stomach region 505, the tether 120 traverses through the pylorus area 510, and the intra-duodenal balloon 125 resides in the patient's duodenum region 515. FIG. 5A shows the intragastric fluid transfer device in an exemplary state when the patient's stomach is not contracting (e.g., in equilibrium). FIG. 5B shows the intragastric fluid transfer device in an exemplary state when the patient's stomach is contracting (putting pressure on the gastric balloon 105), and therefore illustrates the inflatable stimulation device 125 as inflated and pressuring the inner walls of the patient's duodenum 520.

Figure 6A:
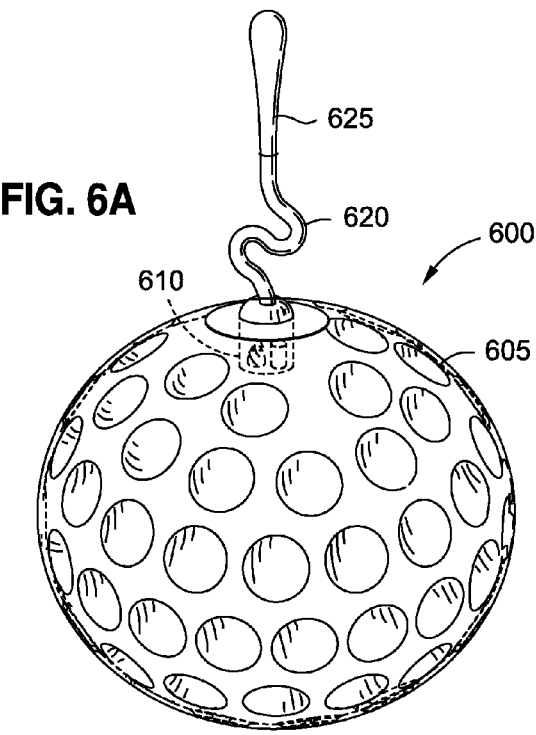
FIG. 6A illustrates the intragastric fluid transfer device with surface recesses in accordance with one or more embodiments described herein.
Figure 6C:
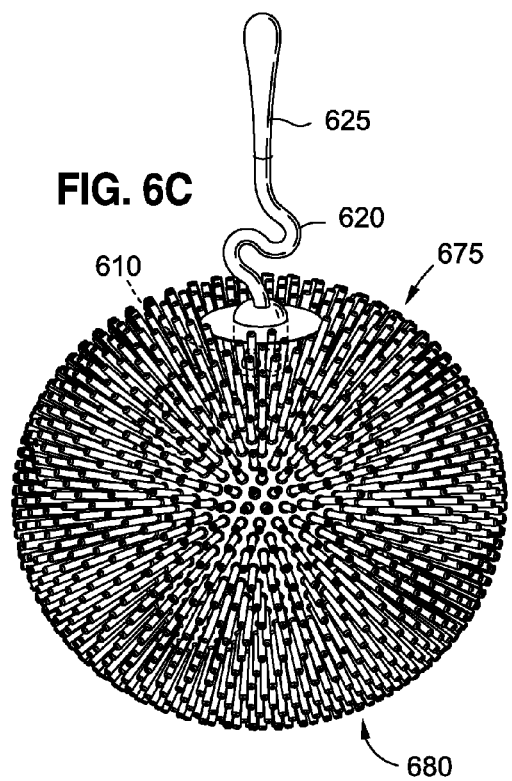
FIG. 6C illustrates the intragastric fluid transfer device with surface extensions in accordance with one or more embodiments described herein.
Figure 6B:
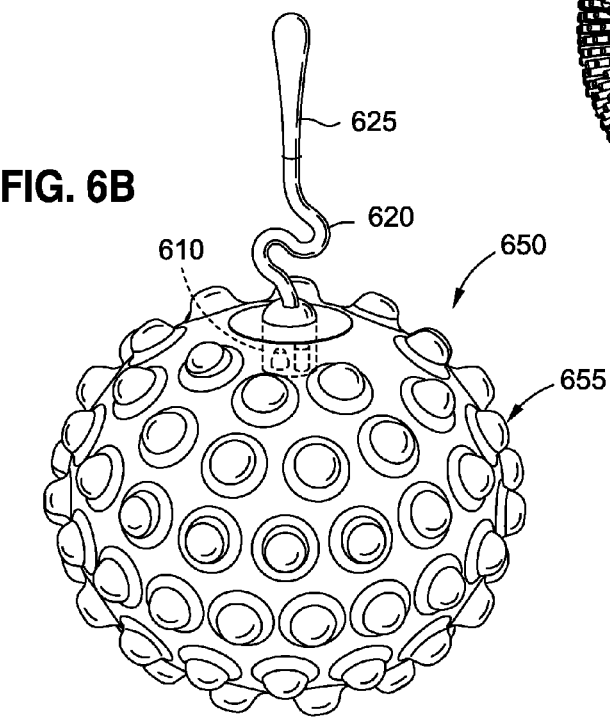
FIG. 6B illustrates the intragastric fluid transfer device with surface protrusions in accordance with one or more embodiments described herein.

In one embodiment, the surface of the intragastric fluid transfer device 100 may be smooth as shown in FIG. 1A. In another embodiment, the surface may include additional satiety triggering features. FIGS. 6A-6C illustrate some examples of the intragastric fluid transfer device with protrusions, recesses and quill-like extensions. For example, as shown in FIG. 6A, the surface of the gastric balloon of the intragastric fluid transfer device 600 may include a plurality of dimples or recesses 605. In another example, FIG. 6B illustrates an intragastric fluid transfer device 650 with a plurality of bumps or protrusions 655. In yet another example, FIG. 6C illustrates an intragastric fluid transfer device 675 with a plurality of quill-like extensions 680.

The intragastric fluid devices 600, 650 and 675 may also include fluid transfer components 610, a tether 620 and an inflatable intra-duodenal balloon 625 which may operate in a similar fashion as the fluid transfer components 110, the tether 120 and the intra-duodenal balloon 125 of FIG. 1A.

As described, the terms "inflated" and "deflated" are meant in relationship to a maximum inflation and maximum deflation state. That is, for example, when the gastric balloon 105 is described to be "inflated", what is meant is that it is more inflated than when the gastric balloon 105 is in a deflated state, and vice versa. These terms do not imply that the entire gastric balloon 105 is completely inflated or completely deflated. Indeed, in one example, an "inflated" state may mean that the gastric balloon 105 is between 70-100% inflated (in another embodiment between 50-100% inflated) and a "deflated" state may mean that the gastric balloon 105 is between 0-70% inflated (in another embodiment between 0-50% inflated). Similarly, when the terms are used to describe other components or members such as the intra-duodenal balloon 125 of FIG. 1, the terms do not imply that the intra-duodenal balloon is completely inflated or completely deflated.

As discussed herein, the examples describe a fluid filled gastric balloon 105 and an intra-duodenal balloon 125 capable of holding a fluid such as saline. However, the "fill" may instead be a different liquid such as water or natural stomach juices. Alternatively, air or another gas may be substituted.

Figure 7:
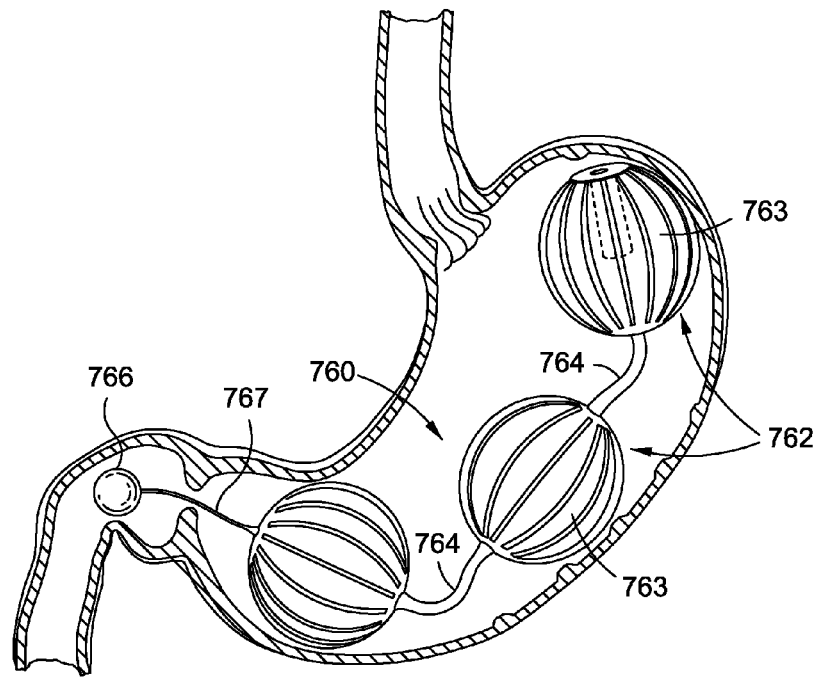
FIG. 7 shows an intragastric device including three tethered inflated balls within the stomach cavity connected to an anchor within the duodenum.

Another space-occupying satiety-inducing device 760 of the present application is shown in FIG. 7, and comprises a plurality of inflated balls 762 linked in series and having slots or flutes 763 thereon. In the illustrated embodiment, there are three inflated balls 762 linked by two intermediate tethers 764. The balls 762 preferably have semi-rigid walls that do not require fluid-pressurizing, although fluid such as saline fills the hollow cavities within each ball. This device 760 is intended to be placed in the stomach, transorally, without invasive surgery, and without associated patient risks of invasive surgery. Recovery time is thought to be minimal, as no extensive tissue healing is required. A one year or longer implant period is targeted, as product life span is material-dependent upon long-term survivability within acidic stomach environment.

Figure 8:
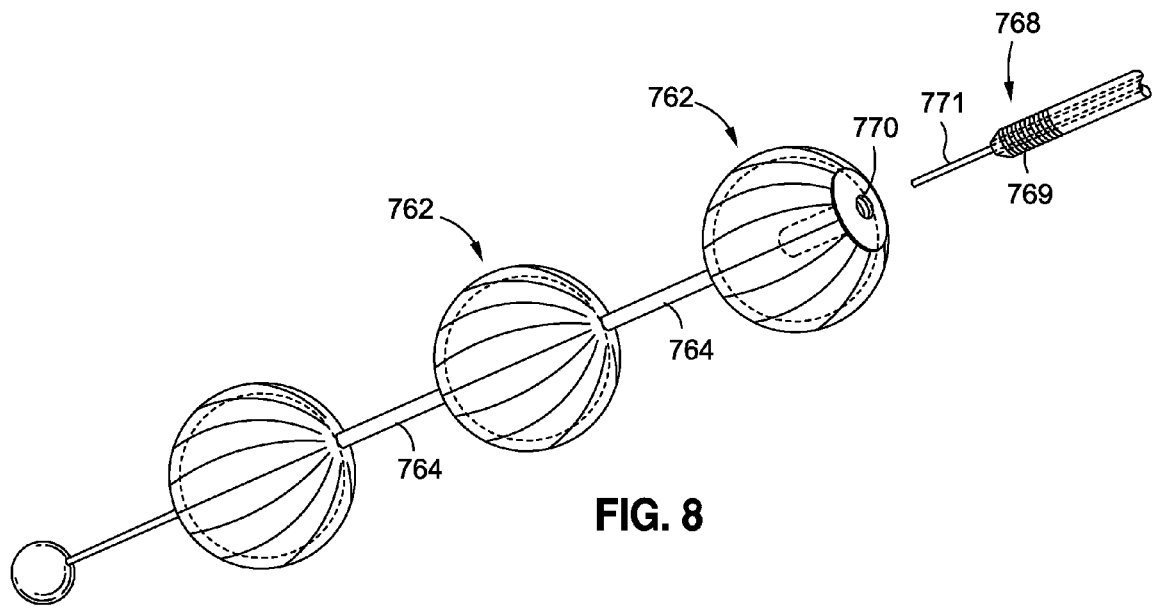
FIG. 8 is an exploded perspective view of the device of FIG. 7 and an exemplary delivery obturator.
Figure 11:
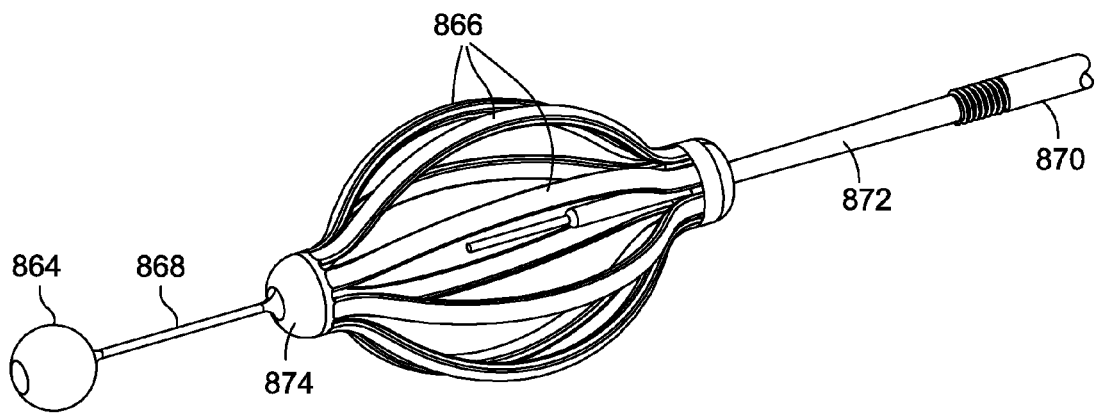
FIG. 11 is a perspective view thereof.

In addition to the embodiment shown in FIGS. 7 and 8, a number of other similar embodiments through FIG. 11 are also shown. In all cases, structure occupies space in the stomach or stimulates stomach wall nerves, while in some cases the devices 760 also delay gastric emptying so food passing through the pylorus into the duodenum takes longer than usual. Both events are thought to precipitate early feelings of satiety. Through these means, additional ingestion later during any single meal is not as likely to be desired.

In the first embodiment of FIGS. 7 and 8, a stainless steel ball 766 attached to the distal end of the device via a tether 767 is small enough to pass through the pyloric sphincter, but because of the size and configuration of the semi-rigid balls 762, they cannot pass through. This serves to retain the ball 766 from descending any further than the length of the tether 767 allows. The ball 766 is thus held in place in the upper duodenum, so food must pass around the ball to exit the stomach, rather than exiting freely, therefore delaying gastric emptying. The tether 767 is sufficiently thin that the pyloric sphincter can easily close around it, so as not to interfere with ordinary stomach processes. It should be noted that though stainless steel is a particularly suitable material for the ball 766, it may be formed from a variety materials with sufficient mass and specific gravity that prevent it from migrating back up through the pyloric sphincter.

Figure 9A:
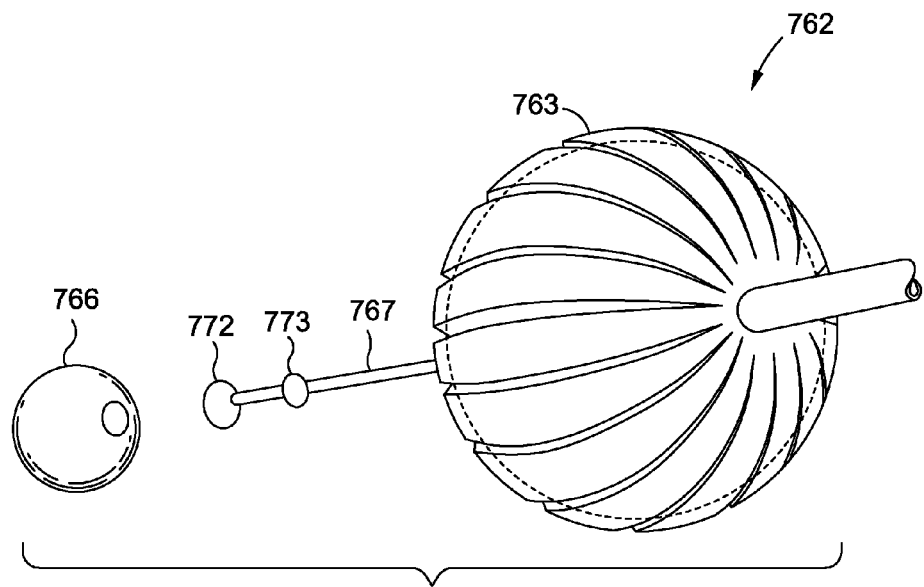
FIGS. 9A and 9B are enlarged perspective views of opposite ends of the exploded view of FIG. 9.
Figure 9B:
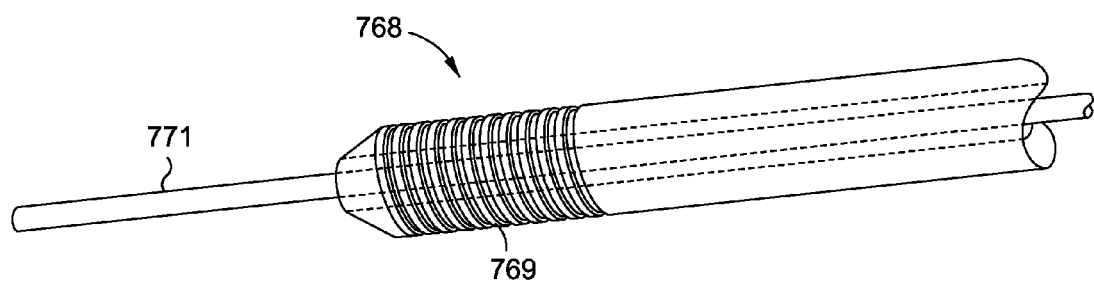

For insertion of the device in FIG. 7, a specially configured, temporary (removable) surgical obturator 768 is used as seen in FIGS. 9 and 9B. A distal end 769 of the obturator 768 threads into a threaded fitting 770 in the proximal ball 762 of the device 760. A stiff wire 771 then extends from the obturator 768 in through the series of connected balls 762. The operator pushes the wire 771 against the inside of the distal ball 762 of the device 760, thereby elongating and compressing the assembly of balls so it can fit comfortably down the esophagus. Because the balls 762 are not pressurized, they elongate to a more oval shape when the wire 771 stretches the assembly. In one embodiment, the balls 762 have expanded diameters of between 30-32 mm, and may be compressed by elongation to between 9-10 mm. The weight of the stainless steel ball 766 causes it to migrate through the pyloric sphincter and "seat" in the upper duodenum, thereby anchoring the distal end of the device 760.

For device removal, the operator re-introduces the obturator 768 along with its central wire 771 down the esophagus into the stomach. Radiopaque rings surrounding both the threads in the fitting 770 of the device 760 and threads 769 of the obturator 760 guide the operator so that the mating elements can be aligned and threaded together. Then the operator presses the wire 771 on the inside of the distal ball 762, thereby elongating and compressing the device 760 so it can be pulled comfortably up the esophagus and out the mouth, dragging the steel ball along.

FIG. 9A illustrates one configuration for anchoring the steel ball 766 in place. In particular, the distal tether 767 includes a heat formed distal end 772 and a second heat formed bead 773 just proximal to the steel ball 766. The proximal bead 773 may be formed first, and the steel ball 766 inserted over the tether 767, whereupon the distal bead 772 is formed.

Another device that induces satiety primarily slows the emptying of stomach contents passing through the pylorus into the duodenum. It is thought that delaying of gastric emptying will increase the length of time that satiety is felt, since food remains longer in the stomach. In that way, additional ingestion during a single meal is not as likely to be desired. Several embodiments disclosed herein perform such a function in addition to occupying space or stimulating the cardia.

Figure 10:
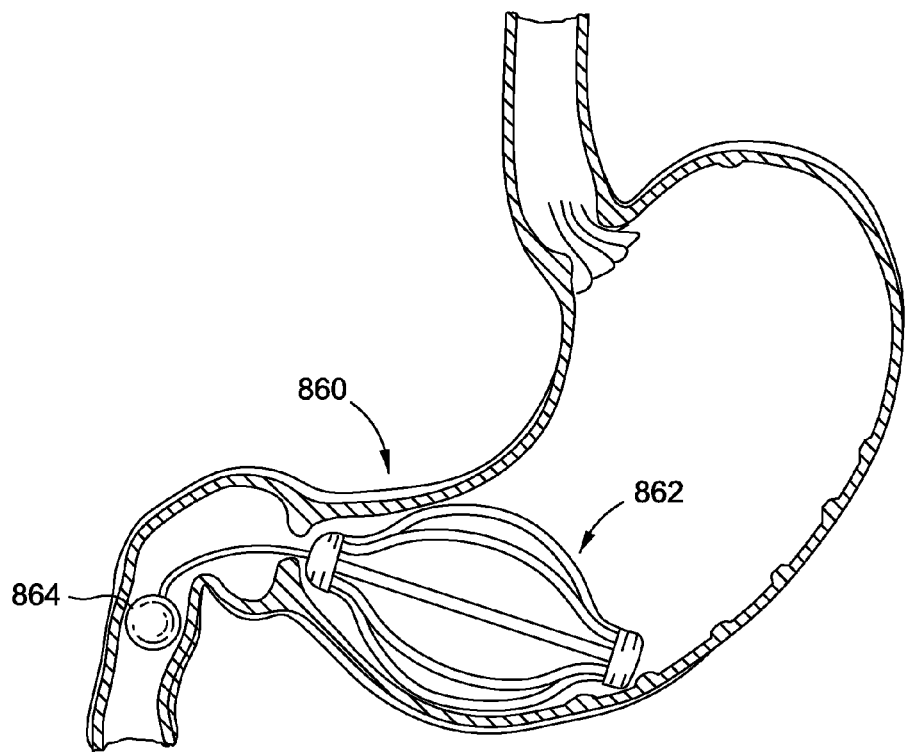
FIG. 10 illustrates an expandable umbrella having a duodenal anchor.

One such device 860 shown in FIGS. 10 and 11 includes a duodenal expandable umbrella frame 862 with an anchor 864. The umbrella frame 862 comprises a compressible grouping of struts 866 (like a folded umbrella) that, in their normal, as-molded configuration, form an oblong structure as seen that is too large to fit through the pylorus, so obstruction in the duodenum is not possible. A stainless steel ball tethered to the distal end of the umbrella frame 862 forms the anchor 864 and is small enough to pass through the pylorus, but since the strut configuration 866 cannot pass through, the ball cannot descend any further than the length of a tether 868 allows. The ball 864 is thus held in place in the upper duodenum, so food must pass around the ball to exit the stomach, rather than exiting freely.

For device insertion, a specially configured, temporary (removable) surgical obturator 870 threads into the umbrella frame 862, and a stiff wire 872 running through the hollow obturator may be pushed against the inside of a distal end 874, thereby elongating and compressing the umbrella frame so it can fit comfortably down the esophagus. The weight of the stainless steel ball 864 causes it to migrate through the pylorus and "seat" in the upper duodenum.

For device removal, the obturator 870 with its central wire 872 is re-introduced down the esophagus into the stomach, and radio opaque rings surrounding both the obturator threads 874 and threads of the obturator (not shown) facilitate alignment and threading connection. Then the wire 872 is pressed to bear on the inside of the distal end 874, thereby elongating and compressing the umbrella frame 862 so it can be pulled comfortably up the esophagus and out the mouth, pulling the steel ball along.

FIG. 12 shows a further intragastric device 920 implanted in the stomach with an inflated balloon 922 tethered to a ribbed duodenal sleeve 924. The intragastric device 920 may be implanted transorally through the esophagus and into the stomach and duodenum, as described above. The device 920 is designed to be located across the pyloric sphincter with the balloon 922 located in the stomach and the sleeve 924 within the duodenal cavity/upper intestinal tract. At the conclusion of treatment, the device 920 is retrieved gastro-endoscopically. The sleeve 924 limits the absorption of nutrients within the duodenum (i.e., induces malabsorption). The balloon 922 occupies space within the stomach, thus limiting the amount of food that can be ingested in a single sitting and inducing satiety. Furthermore, the device may stimulate both the stomach and the duodenum, which further induces feelings of satiety.

The sleeve 924 may comprise a spiral wire embedded in a flexible wall, or may comprise a series of circular loops or rings 926 embedded within a sleeve walls 928, as shown in FIG. 13A. The length of the sleeve 924 is desirably at least 15 inches (38.1 cm). The longer the sleeve 924, the more malabsorption in the duodenum takes place. However, longer sleeves increase the difficulty when implanting and explanting. The reinforcing rings 926 prevent kinking of the sleeve 924, thus ensuring passage of food therethrough. The relative spacing of the rings 926 is dependent on their diameter, and in particular the spacing between the rings should be less than the diameter of the sleeve 924. If the sleeve 924 begins to twist and kink, two adjacent rings 926 will move closer to each other. Once the two rings 926 engage each other, the nascent kink can no longer propagate and the sleeve remains open. Furthermore, the rings are sufficiently close together such that the sleeve cannot fold back on itself. At the same time, the spacing between the rings 926 enables the sleeve 924 to flex and be guided through the sometimes tortuous intestines.

The reinforcing rings 926 are sufficiently rigid to prevent collapse of the sleeve 924, but not so rigid as to prevent peristaltic contractions from the intestine acting on food passing through the sleeve. Furthermore, the ribbed texture of the outer surface of the sleeve 924 helps prevent migration of the sleeve within the intestines once in place. The rings 926 and sleeve wall 928 may be separate elements, with the former embedded within the latter, or they may be manufactured together as a single piece. Desirably, the sleeve wall 928 is made of materials including rubbers, floral silicones, floral elastomers, thermoplastic elastomers, or combinations thereof. As with a spiral wire, the rings 926 may be formed of a flexible metal such as Nitinol, or even a sufficiently rigid polymer.

The balloon 922 may be filled with saline or water once implanted into the stomach cavity. The size of the inflated balloon 922 is such that it cannot pass down the pylorus or back up through the esophageal sphincter. Other than that size requirement, the balloon 922 may be formed in any size or shape. A valve component 930 is provided in the side of the balloon to allow for filling of the device after implantation. The valve 930 may double as a port through which fluid may be drained from within the balloon at the time of explantation.

The balloon 922 attaches to a proximal end of the sleeve 924 using a tether 932. The tether 932 should be made of a material that resists significant elongation. For example, the tether may be made with a material such as strong yet flexible metal or plastic in combination with an outer sheath made of a softer material (e.g., silicone) which provides protection from the stomach acids. The tether 932 should be thin and flexible enough such that its placement across the pyloric sphincter does not impede the anatomical function thereof. At the same time the tether 932 should be strong enough to avoid failure when placed in tension by opposite movements of the balloon 922 and sleeve 924.

It should also be stated that any of the embodiments described herein may utilize materials that improve the efficacy of the device. For example, a number of elastomeric materials may be used including, but not limited to, rubbers, fluorosilicones, fluoroelastomers, thermoplastic elastomers, or any combinations thereof. The materials are desirably selected so as to increase the durability of the device and facilitate implantation of at least six months, and preferably more than 1 year.

Material selection may also improve the safety of the device. Some of the materials suggested herein, for example, may allow for a thinner wall thickness and have a lower coefficient of friction than the current device which may aid in the natural passage of the balloon through the GI tract should the device spontaneously deflate.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:
Silicone materials used include 3206 silicone for any shells, inflatable structures, or otherwise flexible hollow structures. Any fill valves will be made from 4850 silicone with 6% $BaSO_4$. Tubular structures or other flexible conduits will be made from silicone rubber as defined by the Food and Drug Administration (FDA) in the Code of Federal Regulations (CFR) Title 21 Section 177.2600.

Purposes:
the devices are for human implant,
the devices are intended to occupy gastric space while also applying intermittent pressure to various and continually changing areas of the stomach;
the devices are intended to stimulate feelings of satiety, thereby functioning as a treatment for obesity.

General implant procedures:
The device is intended to be implanted transorally via endoscope into the corpus of the stomach.
Implantation of the medical devices will occur via endoscopy.
Nasal/Respiratory administration of oxygen and isoflurane to be used during surgical procedures to maintain anesthesia as necessary.
One exemplary implant procedure is listed below.
a) Perform preliminary endoscopy on the patient to examine the GI tract and determine if there are any anatomical anomalies which may affect the procedure and/or outcome of the study.
b) Insert an introducer into the over-tube.
c) Insert a gastroscope through the introducer inlet until the flexible portion of the gastroscope is fully exited the distal end of the introducer.
d) Leading under endoscopic vision, gently navigate the gastroscope, followed by the introducer/over-tube, into the stomach.
e) Remove gastroscope and introducer while keeping the over-tube in place.
f) OPTIONAL: Place the insufflation cap on the over-tubes inlet, insert the gastroscope, and navigate back to the stomach cavity.
g) OPTIONAL: Insufflate the stomach with air/inert gas to provide greater endoscopic visual working volume.
h) Collapse the gastric implant and insert the lubricated implant into the over-tube, with inflation catheter following if required.
i) Under endoscopic vision, push the gastric implant down the over-tube with gastroscope until visual confirmation of deployment of the device into the stomach can be determined.
j) Remove the guide-wire from the inflation catheter is used.
k) If inflated: Inflate the implant using a standard BioEnterics Intragastric Balloon System ("BIB System") Fill kit.
l) Using 50-60 cc increments, inflate the volume to the desired fill volume.
m) Remove the inflation catheter via over-tube.

n) Inspect the gastric implant under endoscopic vision for valve leakage, and any other potential anomalies. Record all observations.
o) Remove the gastroscope from over-tube.
p) Remove the over-tube from the patient.
End Point Criteria:
Weight Loss
Comprehensive Metabolic Panel (CMP)
HbA1C
Lipid Panel
Tissue Samples/Response Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. An implantable device configured to be placed in a patient's stomach and duodenum region transorally without surgery to treat and prevent obesity, comprising:
   an inflatable gastric balloon defining an inflatable space and residing in the patient's stomach and formed of a material that can withstand the acidic environment of the patient's stomach for at least 6 months, the gastric balloon having an inflated volume sufficient to ensure that the gastric balloon cannot pass through patient's pylorus;
   an inflatable intra-duodenal balloon defining an inflatable space and having a deflated volume that will fit within the patient's duodenum and allow food to pass and an inflated volume that contacts the walls of the duodenum;
   a fluid transfer conduit coupled between the inflatable space of the gastric balloon and the inflatable space of the intra-duodenal balloon; and
   a first valve located between, and in fluid communication with, the inflatable space of the gastric balloon and the inflatable space of the intra-duodenal balloon, the first valve configured to allow fluid to flow freely from the inflatable space of the gastric balloon to the fluid transfer conduit and limit backflow of fluid from the fluid transfer conduit to the inflatable space of the gastric balloon.

2. The device of claim 1, wherein the first valve is a duckbill valve.

3. The device of claim 1, wherein the first valve is configured to limit backflow back into the gastric balloon to 0.2 cubic centimeters per hour.

4. The device of claim 1, further comprising a flow restrictor located between the gastric balloon and intraduodenal balloon, the second valve configured to allow fluid to flow from the intra-duodenal balloon to the gastric balloon only when the pressure within the intra-duodenal balloon exceeds the pressure within the gastric balloon.

5. The device of claim 1, wherein the flow restrictor limits flow back into the gastric balloon to a flow rate of between 0.1 μL per hour to about 1 L per hour.

6. The device of claim 1, wherein the gastric balloon is configured to maintain a volume of 200 milliliters or more to prevent the gastric balloon from migrating into a pylorus region of the patient.

7. The device of claim 1, wherein the gastric balloon has an uneven surface feature that provides stimulation to the stomach walls.

8. A passive intragastric obesity treatment implant, comprising:
   a series of inflatable members connected together with intermediate tethers, each of the inflatable members having slots or flutes on their external surfaces, the inflatable members each having a size that will not pass through the pyloric sphincter and together taking up volume within the stomach of at least 400 ml and being made of a material that will resist degradation over a period of at least six months within the stomach; and
   a duodenal anchor connected to a distal inflatable member with a distal tether, the duodenal anchor having a size that permits it to pass through the pyloric sphincter and be formed of a material of sufficient mass and specific gravity that prevents it from migrating back up through the pyloric sphincter.

9. The implant of claim 8, wherein a proximal inflatable member includes an internally threaded sleeve suitable for receiving an externally threaded end of a delivery tube.

10. The implant of claim 8, wherein the intermediate tethers are tubular permitting passage of a stiff rod through the series of inflatable members.

11. The implant of claim 8, wherein the distal tether includes a heat formed distal end and a second heat formed bead just proximal to a steel ball to retain the steel ball thereon.

12. A passive intragastric obesity treatment implant, comprising:
   an expandable frame formed of a plurality of longitudinally extending struts, the struts being circumferentially spaced apart on a common circumference, and the frame having an expanded diameter sufficient to prevent passage through the pyloric sphincter;
   a tether connected to a distal end of the frame; and
   a duodenal anchor connected to one end of the tether, the duodenal anchor having a size that permits it to pass through the pyloric sphincter and be formed of a material of sufficient mass and specific gravity that prevents it from migrating back up through the pyloric sphincter,
   the implant being formed of a material which permits it to be compressed into a substantially linear delivery configuration and that will resist degradation over a period of at least six months within the stomach.

13. The implant of claim 12, wherein the frame in its expanded state has an oblong shape.

14. The implant of claim 12, wherein the duodenal anchor comprises a stainless steel ball.

15. The implant of claim 12, wherein the frame has a hollow threaded proximal end to which an obturator may attach for delivering and removing the frame.

16. A passive intragastric obesity treatment implant, comprising:
   an inflatable member having an inflated size sufficient to occupy space within the stomach and preventing passage down the pylorus or back up through the esophageal sphincter;
   a ribbed duodenal sleeve for positioning in the duodenum and being reinforced to prevent kinking, wherein the duodenal sleeve comprises a flexible sleeve wall reinforced by a plurality of longitudinally spaced loops, wherein the longitudinal spacing between adjacent loops is less than a diameter of the loops; and
   a tether attaching the duodenal sleeve to the inflatable member, the implant being formed of a material which permits it to be compressed into a substantially linear delivery configuration and that will resist degradation over a period of at least six months within the stomach.

17. The implant of claim 16, wherein the inflatable member further includes a valve member for filling and emptying the member with a fluid.

18. The implant of claim 16, wherein the tether comprises a strong inner member coated with a material that resists degradation in the stomach.

19. The implant of claim 12, wherein the struts define a plurality of longitudinally extending openings in the frame between the struts.

20. The implant of claim 12, wherein the struts are discrete, elongated members.

* * * * *